United States Patent [19]

Ogawa et al.

[11] Patent Number: 4,844,916

[45] Date of Patent: Jul. 4, 1989

[54] DISTURBING AGENT AGAINST INTERCOMMUNICATION BETWEEN DIFFERENT SEXES OF INSECTS

[75] Inventors: Kinya Ogawa, Kanagawa; Akira Yamamoto, Niigata, both of Japan

[73] Assignee: Shin-Etsu Chemical Co., Ltd., Tokyo, Japan

[21] Appl. No.: 187,377

[22] Filed: Apr. 28, 1988

[51] Int. Cl.$^4$ ............................................. A01N 25/08
[52] U.S. Cl. ................................... 424/409; 424/408; 424/405; 424/84
[58] Field of Search ................... 424/84, 405, 408, 409

[56] References Cited

FOREIGN PATENT DOCUMENTS 7009705 1/1982 Japan ..................................... 424/84

OTHER PUBLICATIONS

Carde, R. T., "Attraction of Redbanded Leafroller to Blends of (Z)-and (E)-11-Tridecenyl Acetates", *Journal of Chemical Ecology*, 3(2), 143-9.

*Primary Examiner*—Thurman K. Page
*Assistant Examiner*—P. L. Prater
*Attorney, Agent, or Firm*—Hopgood, Calimafde, Kalil, Blaustein & Judlowe

[57] ABSTRACT

In the technology of population control of lepidopteral insects as an agricultural or horticultural pest, such as tomato pinworms, by distributing dispensers of sex pheromone of the species over the field, an unexpected discovery has been made that, to the contrary to the general understanding for the effectiveness of the E-isomer of the pheromone compound, e.g., 4-tridecenyl acetate, a rather higher activity can be obtained by using a mixture of the E-isomer and Z-isomer in a mixing proportion of 1:1 to 3:1 than the E-isomer in a high purity.

4 Claims, No Drawings

DISTURBING AGENT AGAINST INTERCOMMUNICATION BETWEEN DIFFERENT SEXES OF INSECTS

BACKGROUND OF THE INVENTION

The present invention relates to a disturbing agent against intercommunication between different sexes of insects. More particularly, the invention relates to an effective preparation of a sex pheromone compound as a disturbing agent against intercommunication between different sexes of certain lepidopteral insects, such as tomato pinworms (*Keiferia lycopersicella*) for the purpose of population control.

It is an already established technology in agriculture and horticulture to control the population of pest insects by utilizing the sex pheromone of the particular species of the insects which acts as a disturbing agent against intercommunication between different sexes of the species.

As is known, for example, most of the sex pheromones of various lepidopteral insects, such as tomato pinworms, light-brown apple worms, omnivorous leaf rollers, peach twig borers, spiny bollworms and the like as notorious pests in agriculture are chemically each an aliphatic alcohol having at least one double bond or an acetic acid ester or aldehyde derived from the alcohol. These aliphatically unsaturated compounds each have geometrical isomers including the E-isomer and Z-isomer relative to the steric configuration at the double bond. It is known that the E-isomers only play an important role in the activity of the compound as the sex pheromone of the insects so that it would be desirable that the preparation of a sex pheromone contains the E-isomer in a purity as high as possible in order that an increased activity of disturbing the intercommunication between different sexes of the insects can be obtained.

There is, however, no known industrial method which is generally applicable to the selective preparation of the E-isomers of these sex pheromone compounds. For example, usual methods for the synthesis of these unsaturated organic compounds lead to the formation of substantially the Z-isomer alone so that the desired E-isomer must be prepared by the isomerization treatment of the Z-isomer followed by separation of the isomers, for example, by the urea separation method. Alternatively, the Birch's method of reducing reaction is applicable. Each of these methods is far from industrial applicability due to the very low productivity of the desired E-isomers. This is the reason for the use of sex pheromone preparation which is a mixture of the E- and Z-isomers mainly composed of the E-isomer in admixture with an unavoidable minor amount of the Z-isomer in an object of population control of pest insects for which only the E-isomer is effective according to the generally accepted understanding.

As is mentioned above, it is an extremely difficult matter to industrially prepare an E-isomer of such an unsaturated compound in a sufficiently high purity so that E-isomers of high purity are available only as an extremely expensive chemical reagent. Needless to say, such an extremely expensive chemical reagent cannot be used in the agricultural and horticultural applications as a sex pheromone preparation for population control of pests. Accordingly, conventional sex pheromone preparations under practical applications are usually composed of the E-isomer and the Z-isomer as a mixture in such a proportion that, as a rough measure, the content of the E-isomer is at least 4 times of that of the Z-isomer.

SUMMARY OF THE INVENTION

The present invention accordingly has an object to provide a less expensive but more effective sex pheromone preparation of pests than conventional sex pheromone preparations composed mainly of the E-isomer with admixture of a minor unavoidable amount of the Z-isomer. The present invention has been completed as a result of the extensive investigations undertaken with this object arriving at a quite unexpected discovery that, contrary to the general technical understanding in the prior art, a sex pheromone preparation of pest insects exhibits a rather higher activity to attract a particular sex of the insects than conventional ones when the preparation is a mixture of E- and Z-isomers containing the E-isomer in a relatively low proportion.

Namely, the sex pheromone preparation provided by the invention is a mixture of the E-isomer and Z-isomer of a sex pheromone compound which is a compound having at least one ethylenically unsaturated double bond with geometrical isomers relative to the ethylenically unsaturated double bond of which the proportion of the contents of the E-isomer to the Z-isomer is in the range from 1:1 to 3:1.

DETAILED DESCRIPTION OF THE PREFERRED EMBODIMENTS

The sex pheromone compound to which the principle of the present invention is applicable is a compound having geometrical E- and Z-isomers relative to an ethylenically unsaturated double bond in the molecular structure including, for example, 4-tridecenyl acetate of which the E-isomer is a known sex pheromone of tomato pinworms, 11-tetradecenyl acetate of which the E-isomer is a known sex pheromone of light-brown apple worms and omnivorous leaf rollers, 5-decenyl acetate and 5-decenyl alcohol of which each E-isomer is a known sex pheromone of peach twig borers, 10,12-hexadecadienal of which the E,E-isomer is a known sex pheromone of spiny bollworms and the like.

In contrast to the generally accepted understanding in the prior art that the sex pheromone preparations to be used for the population control of pests should contain the E-isomer of the respective unsaturated organic compound in a proportion as high as possible, the sex pheromone preparation of the invention must contain the Z-isomer in a relatively high, specified proportion relative to the E-isomer. Thus, it is essential in the invention that the sex pheromone preparation should contain the E-isomer and the Z-isomer in a proportion in the range from 1:1 to 3:1. When the proportion of the E-isomer is smaller than the above specified range, the sex pheromone preparation would have a relatively poor activity for attracting the particular sex of the pests. On the other hand, sex pheromone preparations containing the E-isomer in a higher proportion than above also cannot exhibit the highest activity as desired if not to mention the difficulty encountered in the industrial manufacture of such a mixture of geometrical isomers containing the E-isomer in such a high proportion. The sex pheromone preparation of the invention has an activity of disturbing the intercommunication between different sexes of pests equivalent to or even better than a high-purity E-isomer of the compound. In addition, the inventive sex pheromone preparation exhibits no pest-attracting phenomenon as is sometimes the case with an E-isomer even when the concentration of the compound in the atmospheric air is decreased although the mechanism of this phenomenon is not clear. This unique characteristic property imparts the inventive sex pheromone preparation with a great practical advantage for the population control of the pests along with the much lower costs in the industrial manufacture than the high-purity E-isomer of the compound.

Following are the examples and comparative examples to illustrate the invention in more detail but not to limit the scope of the invention in any way.

EXAMPLE 1

A field test was undertaken in six square areas, i.e. test areas No. 1 to No. 6, of each 0.3 hectare wide in a 1.8 hectares wide tomato garden for disturbing intercommunication between different sexes of tomato pinworms using sex pheromone preparations in the following manner. Thus, six preparations of 4-tridecenyl acetate, of which the E-isomer is a known sex pheromone of tomato pinworms, in different mixing proportions of the E-isomer to the Z-isomer shown in Table 1 below. The isomeric mixtures of which the E:Z ratios were 0.5, 2.0 and 2.3 were prepared by adding the Z-isomer to a mixture of E:Z=2.5 prepared by the isomerization reaction of the Z-isomer. The isomeric mixture of E:Z=18 was prepared by the urea treatment of the above mentioned mixture of E:Z=2.5. Each an 80 mg portion of these preparations was introduced into a polyethylene tube having an inner diameter of 0.8 mm, outer diameter of 1.4 mm and length of 20 cm and the tube was sealed at both ends. A cellophane-based adhesive tape was wound around and applied to a 12 cm long central portion of the tube so as to adequately control the releasing velocity of the pheromone compound through the walls of the thus prepared tubular dispensers.

The thus prepared pheromone dispensers were distributed evenly over the test areas on May 2nd. The number of the pheromone dispensers distributed in each of the test areas was 1000 per hectare in each of No. 1 to No. 4 areas and 500 per hectare in No. 5. The test area No. 6 was for control purpose without using any sex pheromone dispensers. A pheromone trap was installed at the center of each test area and the effectiveness of the distributed pheromone dispensers was evaluated by counting the number of the trapped male moths during July and August. Further, the number of damaged fruits was counted in August and September. The results are shown in Table 1 below. In this table, the number of trapped moths gives an average number of the male moths trapped in one night through the month. A smaller numbr of the trapped male moths means a higher effectiveness of the intercommunication-disturbing activity.

TABLE 1

| Test Area | E:Z ratio | Trapped moths July | Trapped moths August | Damaged fruita, % August | Damaged fruita, % September |
|---|---|---|---|---|---|
| 1 | 18 | 0.0 | 0.0 | 0.1 | 0.2 |
| 2 | 2.3 | 0.0 | 0.0 | 0.0 | 0.0 |
| 3 | 0.5 | 0.3 | 1.4 | 0.8 | 10.2 |
| 4 | 0.0 | 2.7 | 8.2 | 1.5 | 18.0 |
| 5 | 2.5 | 0.0 | 0.2 | 0.0 | 0.1 |
| 6 | — | 4.6 | 15.1 | 1.9 | 22.3 |

The results given in the table above indicate that the highest effect could be obtained in the test areas No. 2 and No. 5 where the mixing proportions of the E-isomer to the Z-isomer in the isomeric mixture of the pheromone compound were 2.3 and 2.5, respectively.

EXAMPLE 2

A field test was undertaken on three square test areas No. 7 to No. 9 of a tomato garden each 1 hectare wide using 4-tridecenyl acetate as the sex pheromone compound of tomato pinworms. Pheromone dispensers were prepared each by filling a polyethylene tube having an inner diameter of 0.7 mm, outer diameter of 1.4 mm and length of 20 cm with 60 mg of a mixture of E-4-tridecenyl acetate and Z-4-tridecenyl acetate in a proportion of 2.0, 15.7 or 0.1 prepared in a similar manner to Example 1 and sealing the tube at both ends. Each tube was coated over a 14 cm long central portion with an emulsion of polyvinylidene chloride.

The thus prepared 800 pheromone dispensers a group were distributed evenly over the respective test areas on April 29 and the number of damaged fruits was counted in September to find that 3.2%, 4.5% and 38.2% of the fruits were damaged in the test areas No. 7, No. 8 and No. 9, respectively. These results also indicate that the best effect could be obtained when the proportion of the E- to Z-isomers was 2.0.

EXAMPLE 3

Three groups of pheromone dispensers were prepared each by filling 1000 polyethylene tubes having an inner diameter of 0.8 mm, outer diameter of 1.4 mm and length of 20 cm each with 80 mg of a mixture of E-11-tetradecenyl acetate and Z-11-tetradecenyl acetate in a proportion of 1.9, 15.7 or 0.7 and sealing at both ends. The isomeric mixture of E:Z =1.9 was obtained by the isomerization reaction of the Z-isomer and the mixture of E:Z =0.7 was prepared by adding the Z-isomer to the mixture of E:Z =1.9. The mixture of E:Z =15.7 was obtained by the urea treatment of the mixture of E:Z =1.9. A field test was undertaken in four square test areas No. 10 to No. 13, of which No. 13 was for control purpose, of a vineyard of each 1 hectare wide by hanging 1000 pheromone dispensers on the vines at a height of about 1 meter from the ground in an even distribution over the area so as to release the pheromone compound, of which the E-isomer is a known sex pheromone of omnivorous leaf rollers, in the dispensers at a rate which was kept substantially uniform over about 2 months. The effectiveness of the thus released sex pheromone compound was evaluated by counting the number of copulations which took place between sexes of the insects by the so-called trapped-female method. The results obtained in the test areas No. 10, No. 11, No. 12 and No. 13 were 2%, 8%, 22% and 82%, respectively, the last value being for control purpose without using the pheromone dispensers. These results indicate that the activity of the sex pheromone compound was outstandingly high when the proportion of the E-isomer to the Z-isomer was 1.9 as compared with the mixtures with the ratios of 15.7 and 0.7.

What is claimed is:

1. A mixture of geometrical isomers of an organic compound having an ethylenically unsaturated double bond in a molecule composed of the E-isomer and the Z-isomer, of which the E-isomer has an activity as a sex pheromone of lepidopteral insects, the mixing ratio of the E-isomer to the Z-isomer in the mixture being in the range from 1:1 to 3:1.

2. A dispenser of sex pheromone of lepidopteral insects for population control thereof which is a plastic-made tube filled with a mixture of the E-isomer and Z-isomer of a sex pheromone compound of the insects which is a compound having at least one aliphatically unsaturated double bond with geometrical isomers relative to the ethylenically unsaturated double bond, the proportion of the contents of the E-isomer to the Z-isomer in the mixture being in the range from 1:1 to 3:1.

3. A dispenser of sex pheromone of tomato pinworms which is a plastic-made tube filled with a mixture of E-tridecenyl acetate and Z-tridecenyl acetate in a proportion in the range from 1:1 to 3:1.

4. A method for controlling the population of tomato pinworms which comprises distributing, in a tomato garden, dispensers each of which is a plastic-made tube filled with a mixture of E-tridecenyl acetate and Z-tridecenyl acetate in a proportion in the range from 1:1 to 3:1.

* * * * *